(12) United States Patent
Sharpe

(10) Patent No.: US 7,012,689 B2
(45) Date of Patent: Mar. 14, 2006

(54) FLOW CYTOMETER WITH ACTIVE AUTOMATED OPTICAL ALIGNMENT SYSTEM

(75) Inventor: Johnathan C. Sharpe, Hamilton (NZ)

(73) Assignee: Dako Colorado, Inc., Fort Collins, CO (US)

( * ) Notice: Subject to any disclaimer, the term of this patent is extended or adjusted under 35 U.S.C. 154(b) by 274 days.

(21) Appl. No.: 10/478,275

(22) PCT Filed: May 17, 2002

(86) PCT No.: PCT/US02/15795

§ 371 (c)(1),
(2), (4) Date: Nov. 17, 2003

(87) PCT Pub. No.: WO02/092247

PCT Pub. Date: Nov. 21, 2002

(65) Prior Publication Data

US 2004/0169867 A1   Sep. 2, 2004

Related U.S. Application Data

(60) Provisional application No. 60/291,736, filed on May 17, 2001.

(51) Int. Cl.
  G01B 11/00 (2006.01)
(52) U.S. Cl. ................................. 356/399
(58) Field of Classification Search ............ 356/72–73, 356/399
  See application file for complete search history.

(56) References Cited

U.S. PATENT DOCUMENTS

| | | | |
|---|---|---|---|
| 3,299,354 A | 1/1967 | Hogg | 207/582 |
| 3,661,460 A | 5/1972 | Elking et al. | 356/36 |
| 3,710,933 A | 1/1973 | Fulwyler et al. | 209/3 |
| 3,761,941 A | 9/1973 | Robertson | 346/1 |
| 3,810,010 A | 5/1974 | Thom | 324/71 |
| 3,826,364 A | 7/1974 | Bonner et al. | 209/3 |
| 3,833,796 A | 9/1974 | Fetner et al. | 235/151.3 |
| 3,960,449 A | 6/1976 | Carleton et al. | 356/103 |
| 3,963,606 A | 6/1976 | Hogg | 209/3 |
| 3,973,196 A | 8/1976 | Hogg | 324/71 |
| 4,014,611 A | 3/1977 | Simpson et al. | 356/72 |
| 4,070,617 A | 1/1978 | Kachel et al. | 324/71 |
| 4,162,282 A | 7/1979 | Fulwyler et al. | 264/9 |
| 4,230,558 A | 10/1980 | Fulwyler | 209/3.1 |
| 4,302,166 A | 11/1981 | Fulwyler et al. | 425/6 |
| 4,317,520 A | 3/1982 | Lombardo et al. | 209/3.1 |
| 4,318,480 A | 3/1982 | Lombardo et al. | 209/3.1 |
| 4,318,481 A | 3/1982 | Lombardo et al. | 209/3.1 |
| 4,318,482 A | 3/1982 | Barry et al. | 209/3.1 |
| 4,318,483 A | 3/1982 | Lombardo et al. | 209/3.1 |
| 4,325,483 A | 4/1982 | Lombardo et al. | 209/3.1 |
| 4,341,471 A | 7/1982 | Hogg et al. | 356/343 |
| 4,350,410 A | 9/1982 | Minott | 350/170 |
| 4,361,400 A | 11/1982 | Gray et al. | 356/23 |
| 4,395,676 A | 7/1983 | Hollinger et al. | 324/71.4 |
| 4,400,764 A | 8/1983 | Kenyon | 362/263 |
| 4,487,320 A | 12/1984 | Auer | 209/3.1 |
| 4,498,766 A | 2/1985 | Unterleitner | 356/73 |
| 4,515,274 A | 5/1985 | Hollinger et al. | 209/3.1 |
| 4,523,809 A | 6/1985 | Taboada et al. | 350/163 |

(Continued)

Primary Examiner—Gregory J. Toatley, Jr.
Assistant Examiner—Isiaka O. Akanbi
(74) Attorney, Agent, or Firm—Santangelo Law Offices, P.C.

(57) ABSTRACT

An automated monitoring and alignment system to position the mechanical and optical components of a flow cytometer to enhance the consistency, performance, and efficiency of particle sorting and analysis applications.

17 Claims, 5 Drawing Sheets

U.S. PATENT DOCUMENTS

Figure 1:
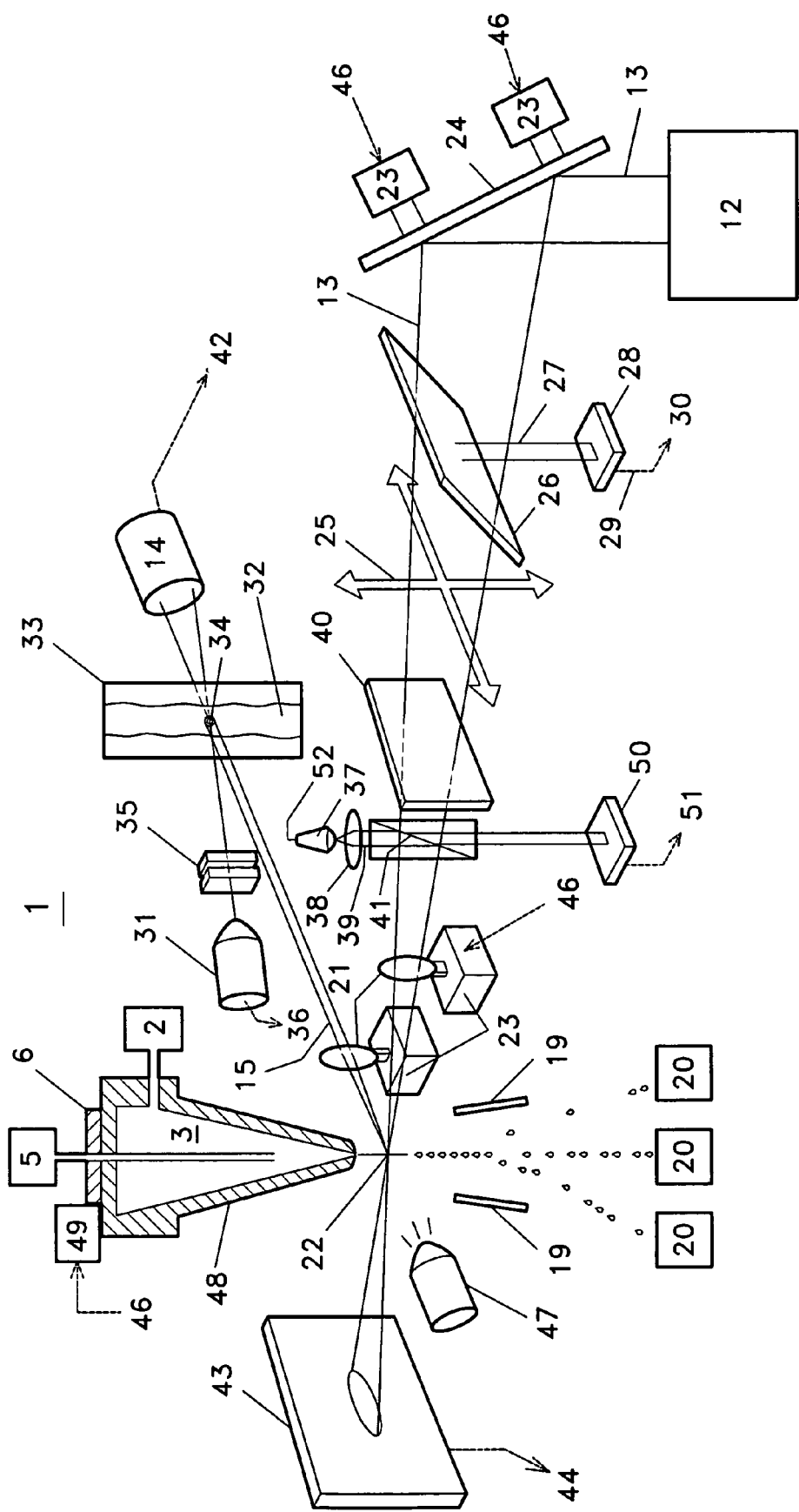

| Patent No. | | Date | Inventor | Class |
|---|---|---|---|---|
| 4,538,733 | A | 9/1985 | Hoffman | 209/3.1 |
| 4,598,408 | A | 7/1986 | O'Keefe | 372/94 |
| 4,600,302 | A | 7/1986 | Sage, Jr. | 356/39 |
| 4,631,483 | A | 12/1986 | Proni et al. | 324/71.4 |
| 4,673,288 | A | 6/1987 | Thomas et al. | 356/72 |
| 4,691,829 | A | 9/1987 | Auer | 209/3.1 |
| 4,702,598 | A | 10/1987 | Böhmer | 356/343 |
| 4,744,090 | A | 5/1988 | Freiberg | 372/94 |
| 4,758,729 | A | 7/1988 | Monnin | 250/560 |
| 4,794,086 | A | 12/1988 | Kasper et al. | 436/36 |
| 4,818,103 | A | 4/1989 | Thomas et al. | 356/72 |
| 4,831,385 | A | 5/1989 | Archer et al. | 346/1.1 |
| 4,845,025 | A | 7/1989 | Lary et al. | 435/2 |
| 4,942,305 | A | 7/1990 | Sommer | 250/574 |
| 4,981,580 | A | 1/1991 | Auer | 209/3.1 |
| 4,983,038 | A | 1/1991 | Ohki et al. | 356/246 |
| 5,005,981 | A | 4/1991 | Schulte et al. | 366/219 |
| 5,007,732 | A | 4/1991 | Ohki et al. | 356/73 |
| 5,030,002 | A | 7/1991 | North, Jr. | 356/317 |
| 5,079,959 | A | 1/1992 | Miyake et al. | 73/864.85 |
| 5,098,657 | A | 3/1992 | Blackford et al. | 422/73 |
| 5,101,978 | A | 4/1992 | Marcus | 209/3.1 |
| 5,127,729 | A | 7/1992 | Oetliker et al. | 356/317 |
| 5,144,224 | A | 9/1992 | Larsen | 324/71.4 |
| 5,150,313 | A | 9/1992 | Van den Engh et al. | 364/569 |
| 5,159,397 | A | 10/1992 | Kosaka et al. | 356/73 |
| 5,159,403 | A | 10/1992 | Kosaka | 356/243 |
| 5,167,926 | A | 12/1992 | Kimura et al. | 422/67 |
| 5,180,065 | A | 1/1993 | Touge et al. | 209/577 |
| 5,182,617 | A | 1/1993 | Yoneyama et al. | 356/440 |
| 5,199,576 | A | 4/1993 | Corio et al. | 209/564 |
| 5,215,376 | A | 6/1993 | Schulte et al. | 366/348 |
| 5,247,339 | A | 9/1993 | Ogino | 356/73 |
| 5,259,593 | A | 11/1993 | Orme et al. | 266/78 |
| 5,260,764 | A | 11/1993 | Fukuda et al. | 356/73 |
| 5,298,967 | A | 3/1994 | Wells | 356/336 |
| 5,359,907 | A | 11/1994 | Baker et al. | 73/865.5 |
| 5,370,842 | A | 12/1994 | Miyazaki et al. | 422/82.06 |
| 5,412,466 | A | 5/1995 | Ogino | 356/246 |
| 5,452,054 | A | 9/1995 | Dewa et al. | 355/67 |
| 5,466,572 | A | 11/1995 | Sasaki et al. | 435/2 |
| 5,467,189 | A | 11/1995 | Kreikebaum et al. | 356/336 |
| 5,483,469 | A | 1/1996 | Van den Engh et al. | 364/555 |
| 5,540,494 | A | * | 7/1996 | Purvis, Jr. et al. | 356/73 |
| 5,558,998 | A | 9/1996 | Hammond et al. | 435/6 |
| 5,596,401 | A | 1/1997 | Kusuzawa | 356/23 |
| 5,601,235 | A | 2/1997 | Booker et al. | 239/4 |
| 5,602,039 | A | 2/1997 | Van den Engh | 436/164 |
| 5,602,349 | A | 2/1997 | Van den Engh | 73/864.85 |
| 5,641,457 | A | 6/1997 | Vardanega et al. | 422/82.01 |
| 5,643,796 | A | 7/1997 | Van den Engh et al. | 436/50 |
| 5,650,847 | A | 7/1997 | Maltsev et al. | 356/336 |
| 5,675,401 | A | 10/1997 | Wangler et al. | 355/67 |
| 5,700,692 | A | 12/1997 | Sweet | 436/50 |
| 5,707,808 | A | 1/1998 | Roslaniec et al. | 435/6 |
| 6,079,836 | A | 6/2000 | Burr et al. | 357/70 |
| 6,263,745 | B1 | 7/2001 | Buchanan et al. | 73/865.5 |
| 6,400,453 | B1 | 6/2002 | Hansen | 356/237.1 |
| 6,819,411 | B1 * | 11/2004 | Sharpe et al. | 356/72 |

* cited by examiner

FLOW CYTOMETER WITH ACTIVE AUTOMATED OPTICAL ALIGNMENT SYSTEM

This application is a United States National Stage Application under 35 U.S.C. 371 of International Application No. PCT/US02/15795, filed May 17, 2002, which claims the benefit of and priority to U.S. Provisional Application No. 60/291,736 filed May 17, 2001, PCT Application PCT/US02/15795 being filed while Original U.S. Application 60/291,736 was pending, each hereby incorporated by reference.

I. TECHNICAL FIELD

An automated monitoring and alignment system to position the mechanical and optical components of a flow cytometer to enhance the consistency, performance, and efficiency of particle sorting and analysis applications.

II. BACKGROUND

Flow cytometry provides a method of analyzing and differentiating particles applicable to various clinical and research applications. Generally, flow cytometer systems irradiate particles and then sense the radiation emitted from the particle in order to identify particular physical attribute(s) of the individual particle(s) being studied. In particle sorting applications, each particle can be separated from the main population based upon the physical attributes identified as disclosed, for example, by U.S. Pat. Nos. 5,643,796; 5,602,349; and 5,602,039; and International Patent Application No. PCT/US95/13308, each hereby incorporated by reference.

During operation of flow cytometers, hydrodynamic focusing entrains particles in a fluid stream so that they can be individually introduced into a target area or analyzing area. The fluid stream may be induced to form droplets to subsequently aid in the separation of individual particles. Typically, flow cytometers use an electromagnetic radiation emission source such as a laser to generate a beam of electromagnetic radiation that can be directionally controlled to intercept the target area. Irradiation of a target particle passing through the target area, such as a cell, can give rise to scatter or fluorescence emission that can be directionally controlled to a receiver that generates a signal that can be analyzed to differentiate particles.

A significant problem with conventional flow cytometer systems can be that precise analysis of such scatter or fluorescence emission requires that the target area remain precisely aligned with the beam of electromagnetic radiation and that the scatter or fluorescence emission from irradiation of the target remain precisely aligned with the sensor. However, the position of the various components of a flow cytometer change in response to small fluctuations in the external environment, including, but not limited to small fluctuations in temperature, pressure, mechanical forces, as well as small fluctuations in the internal environment, including, but not limited to, electronic drift, radiation frequency or amplitude, or the like. The fluctuations can occur during set up of the instrument or during routine instrument operation raising a variety of concerns.

First, the period of time that an operator expends to align a flow cytometer at the start of an operating period or during routine operation of the flow cytometer can be considerable. It can amount to a significant portion of the operator's scheduled time on the instrument and can abbreviate or even preclude any actual analysis efforts.

Second, monitoring of alignment over long time periods, perhaps hours, can be difficult with the naked eye. Even the smallest variations in alignment can render sensor signals useless or result in increased contamination of sorted particle populations. On-the-fly alignment correction by the flow cytometer operator may not be reliable since the data available to the operator can result in subjective estimates of true alignment.

Third, inconsistency from alignment to alignment can prevent satisfactory calibration of flow cytometers to standardized calibration particles. Often instrument parameters other than alignment are used to calibrate an instrument once the optical alignment is subjectively optimized by an operator. Those familiar with flow cytometry may be aware that instrument calibration performed in this manner can lead to a wide and sometimes unacceptable variation in operating results, even during routine applications.

Fourth, because conventional flow cytometer systems may not have the necessary alignment monitoring equipment to determine if a flow cytometry system is aligned, is slightly out of alignment and requires adjustment, or whether the system is catastrophically mis-aligned, it can be difficult to allow a conventional flow cytometer system to operate unattended by an operator.

Various attempts have been made to hard-mount all optical components in conventional flow cytometer systems to address these concerns. Unfortunately, such flow cytometer systems can still be prone to temperature and mechanical drift and need to be serviced regularly for alignment re-calibration. Moreover, hard mount optical components may only be available with respect to certain cuvette-based flow cytometer systems.

As to the field of flow cytometry and the overall desire to automate and monitor mechanical and optical alignment of flow cytometry systems, the present invention discloses techniques that overcome virtually every one of these problems in a practical fashion.

Perhaps surprisingly, it satisfies a long-felt need to achieve high-speed, accurate, and economical methods for automated positioning of components within the flow cytometer. To some degree, even those involved in the manufacturing of flow cytometers had not appreciated that the problems of monitoring and directionally controlling flow cytometer system alignment could be solved by utilizing the various components disclosed in the present invention.

III. DISCLOSURE OF THE INVENTION

The present invention includes a variety of aspects that may be selected in different combinations based upon the particular application or needs to be addressed. In one basic embodiment, the invention discloses a monitoring and alignment control system that uses positional, directional, or image sensing to control the alignment of various components of a flow cytometer.

A further broad object of particular embodiments of the invention can be to allow alignment monitoring during routine operation of a flow cytometer. In keeping with this object, a goal can be to provide an optical image of the target region of the flow cytometer to allow very accurate determination of its position, and that of the electromagnetic radiation sources, such as lasers.

Another object of particular embodiments of the invention can be to permit alignment during normal flow cytometer operation, including but not limited to particle processing. In keeping with this object, a goal is to utilize a control scheme that may be employed without interfering with the flow cytometer processing to provide a very accurate level of alignment precision.

A further object of particular embodiments of the invention can be to permit monitoring without impacting the quality of the measurements made by the flow cytometer system. This object has a goal of providing a non-intrusive monitoring system that uses position sensitive detectors, or illumination sources for imaging purposes that are located in such a way as not to interfere physically, or spectrally, with the optical path of the flow cytometer.

Yet another object of particular embodiments of the invention can be to provide a design that minimizes the space requirements in the vicinity of the sensing region. In keeping with this object, a goal is to utilize as many devices already employed in the flow cytometer (lenses, image-sensing devices, etc.) so as to minimize intrusion and operational complications.

Naturally, further objects of the invention are disclosed throughout other areas of the specification and claims.

IV. BRIEF DESCRIPTION OF THE DRAWINGS

FIG. 1 illustrates a particular embodiment of the invention that uses positional, directional, or image sensing to control of the alignment of various components of a flow cytometer.

Figure 2:
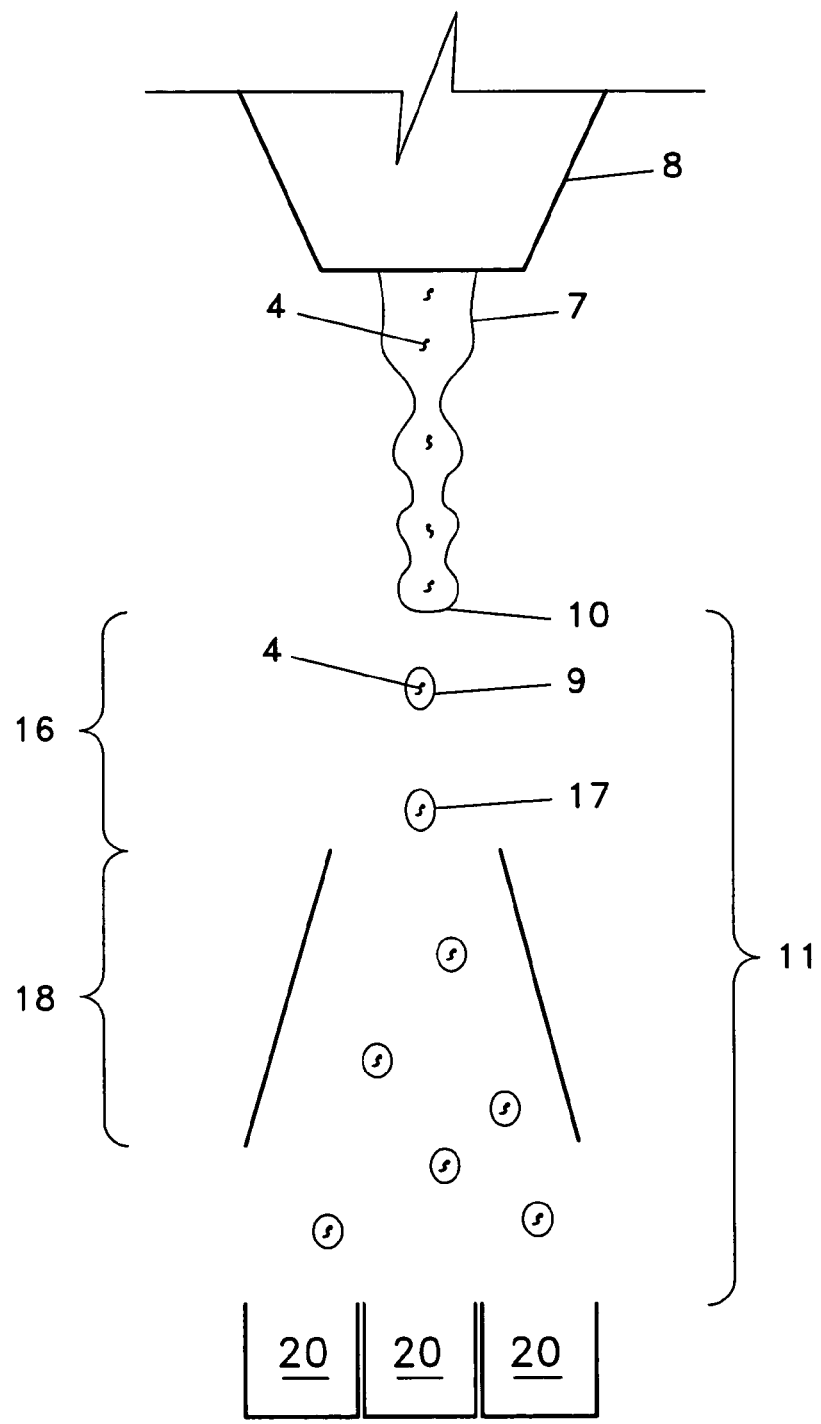

FIG. 2 provides a enlarged view of a particular embodiment of the invention having a fluid stream exiting the tip of a nozzle.

Figure 3:
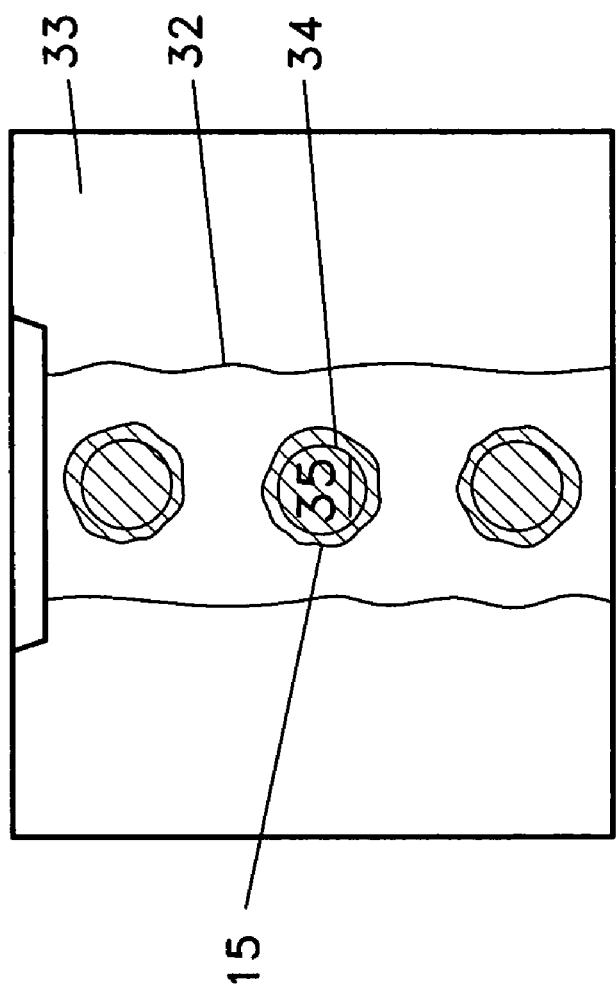

FIG. 3 provides an enlarged view of a particular embodiment of an image screen having screen apertures on which an image representation of a fluid stream and radiation emission pattern is incident.

Figure 4:
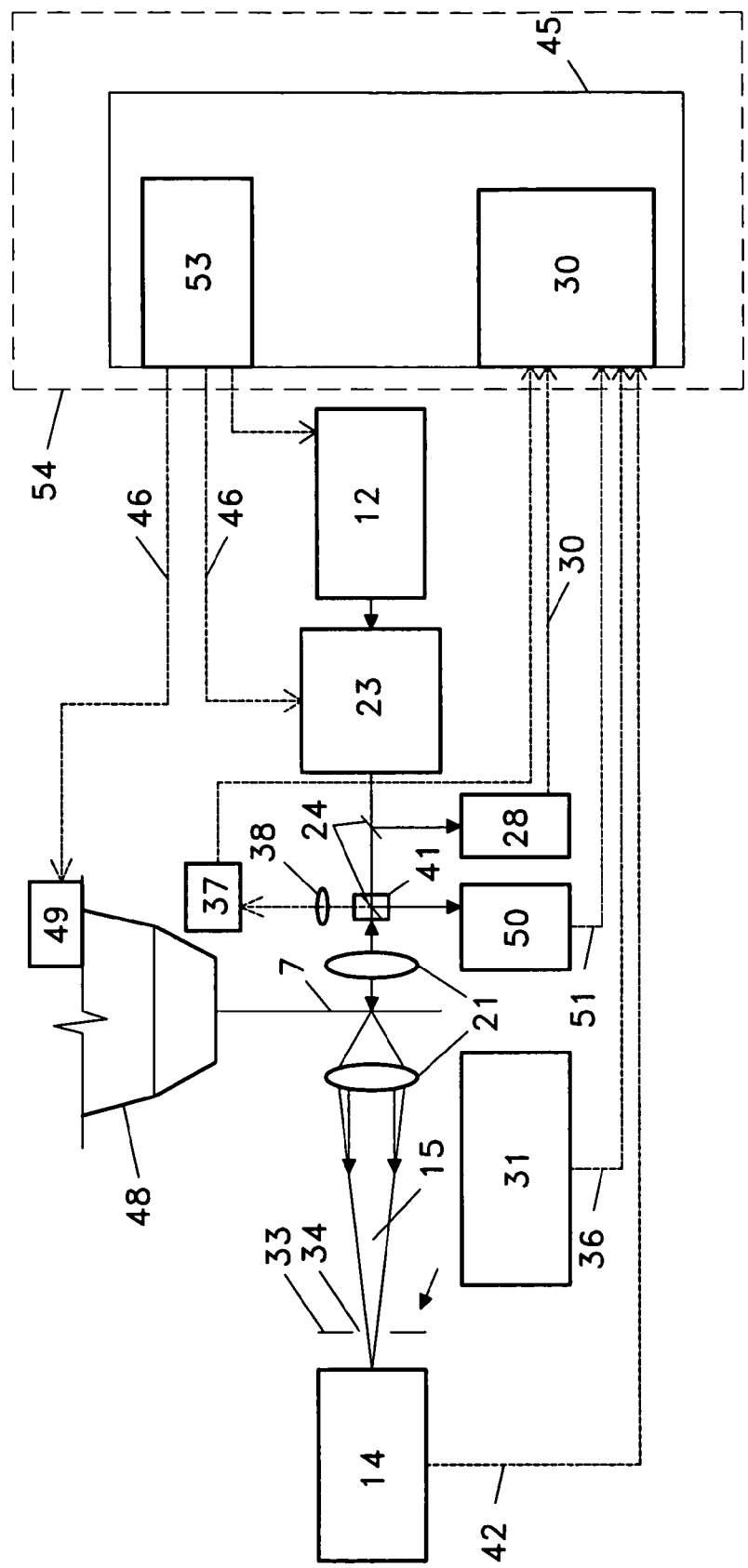

FIG. 4 provides a functional block diagram of a particular embodiment of an alignment control system with respect to the invention.

Figure 5:
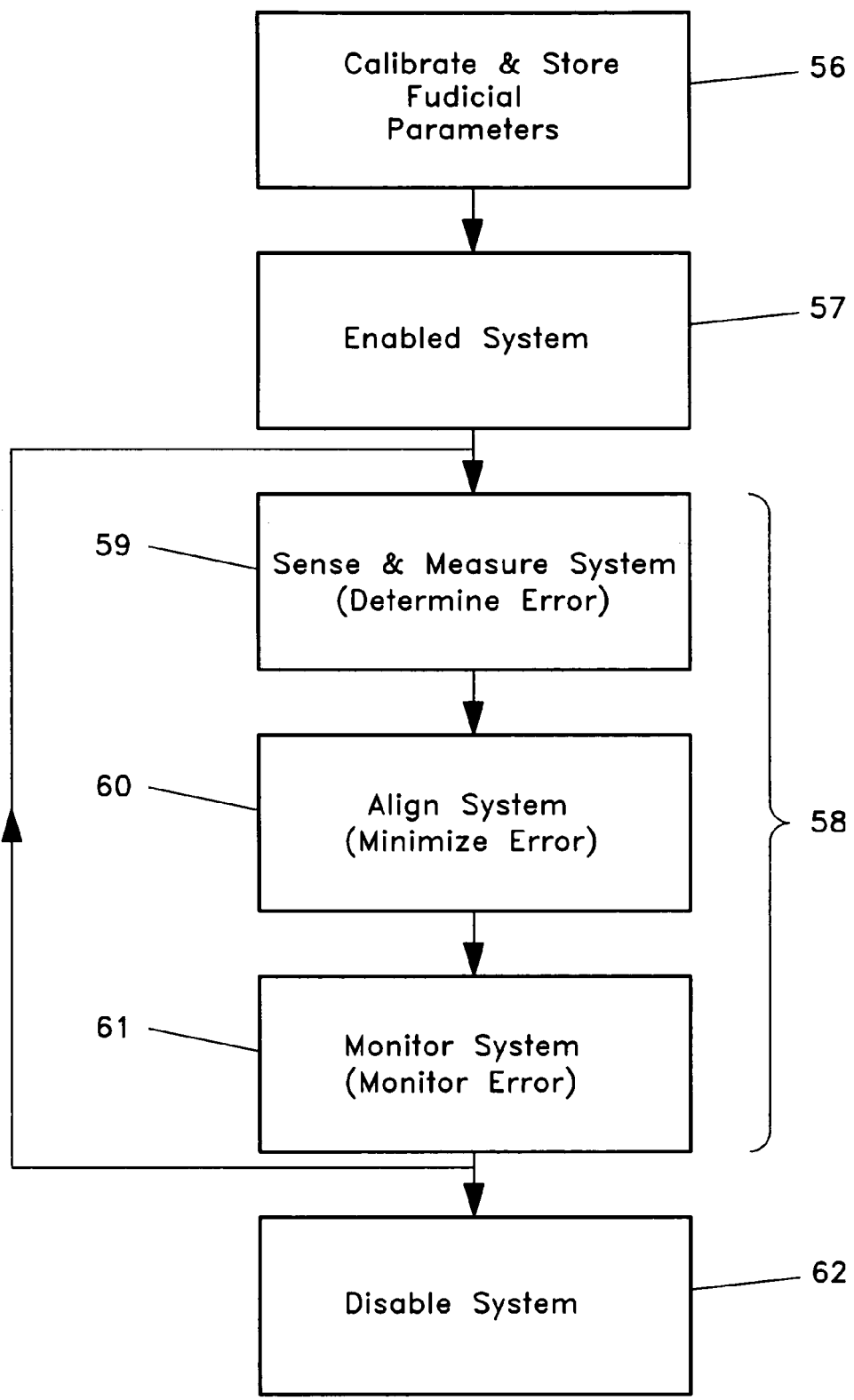

FIG. 5 provides a flow chart of an alignment algorithm in accordance with the invention.

V. MODE(S) FOR CARRYING OUT THE INVENTION

The invention provides an alignment and monitoring system which may be used with regard to various applications. While the description provides detailed examples in the context of droplet or continuous jet flow cytometer application, such examples are not meant to limit the use of the invention to applications in flow cytometry but should be understood to be illustrative of the broad range of applications in which the invention can be used.

Now referring primarily to FIGS. 1 and 2, it can be understood that particular embodiments of the invention can provide an alignment and monitoring system that can be implemented in conjunction with a droplet or continuous jet flow cytometer(s). In a flow cytometer (1) embodiment of the invention, a fluid stream source (2) provides a fluid stream (3) into which particles (4) can be suspended. A source of particles (5) can insert the particles from time to time such that at least one particle becomes entrained in or is hydrodynamically focused in the fluid stream (3). An oscillator (6) responsive to the fluid stream (3) perturbs the fluid stream. A fluid stream (7) entraining particles (4) can then be established below the tip of the nozzle (8) of the flow cytometer. The stream can be established in a steady state condition such that droplets (9) that encapsulate a single particle (4) form and break away from the contiguous part of the stream. When the fluid stream (7) is established in this steady state fashion, a stable droplet break-off point (10) can be established. Below the droplet break-off point (10) a free fall zone (11) can exist. This free fall zone (11) embodies the area where the droplets move once they break away from the contiguous part of the stream. An electromagnetic radiation source (12), such as a laser, that emits an electromagnetic radiation beam (13) and a receiver (14) in combination (or separately), can be used to monitor the fluid stream (7) for a particle (4). The receiver (14) generates a signal (42) in response to incident fluorescent or scatter emission from intercept of the particle (4) with the electromagnetic radiation beam (13).

For example, an a beam of electromagnetic radiation (13), such as a laser beam, emitted from an electromagnetic radiation source (12), such as a laser, can be aimed at the fluid stream (7) to intercept a target (22), such as a particle (4) in the fluid stream (7). Upon irradiation of the target (22), fluorescence or scattered emission (15) can be generated. The fluorescence or scattered emission (15) can be incident to the receiver (14), such as a photomultiplier tube, to generate an emission signal (42) that can be analyzed. Importantly, it should be noted that a plurality of electromagnetic radiation beam paths and florescence or scatter emission paths can exist within a single flow cytometry system each of which can be monitored and directionally controlled by the invention.

Based upon analysis of the emission signal (42) generated by the receiver (14) that corresponds to a flourescent occurrence or a scattered light occurrence, the particle(s)(4) can be differentiated. A droplet charging location (16) can exist at a point along the free fall zone (11). Based upon the type of particle (4), the droplet (9) can be charged positively, negatively, or left uncharged. As the charged droplets (17) fall in the free fall zone, they can pass through an electrostatic field (18). If the droplets have been charged with a positive or negative charge, the electrostatic field (18) established between electrostatic plates (19) can deflect the charged droplets such that the trajectory of the deflected droplets and the trajectory of the neutral droplets serves to separate one type of particle from another. These separated particles can then be collected into container(s) (20).

Now referring primarily to FIG. 1, the invention may further comprise one or more focal element(s)(21) to maximize the intensity of the radiation on the target (22) which can be a location in the fluid stream (7). The focal element (21) can be responsive to a position control element (23) that can allows the focal element (21) to travel (often about the optical axis of the excitation light direction) and maintain focus of the electromagnetic radiation beam (13) or laser beam on the target (22).

In certain embodiments of the invention the beam of electromagnetic radiation (13) emitted from the electromagnetic radiation emission source (12) can be directionally responsive to at least one optical element (24) to direct or steer the electromagnetic radiation beam (13) toward the target area (22). The optical element (24) can comprise one or more reflecting elements, such as mirrors. These optical element(s)(24) can be adjustably mounted to provide variable position or angle, and therefore the direction of the electromagnetic radiation beam (13) can be controlled.

Again primarily referring to FIG. 1, a single partially reflective element (26), or a plurality of partially reflective elements, such as beam splitters, may be located in the path of the electromagnetic radiation beam (13) prior to incidence on the target (22) to sample a portion of the electromagnetic radiation beam (27) to at least one directionally sensitive device (28). The directionally sensitive device(s)(27) can be for example a quadrant photodiode sensor that generates photocurrent in each quadrant. By comparing the photocurrent generated in each quadrant, directional change in two axis (25) can be detected and an electromagnetic radiation beam position signal (30) can be generated, as for example, disclosed by Silicon Sensors, http://www.siliconsensors.com/bpd_a.htm (2000); and Hamatsu, Two-Dimensional PSDs, S5990, S5991, or S4744, (1997), each hereby incorporated by reference herein.

In other embodiments of the invention, a directionally sensitive device (43) can be located such that the beam of electromagnetic radiation is first incident on the target (22) and then incident on the surface of the directionally sensitive device (43). Naturally, in certain embodiments of the invention directionally sensitive devices (28) can be located prior to incidence of the beam of electromagnetic radiation (13) on the target (22) and directionally sensitive devices (43) can be located after incidence of the beam of electromagnetic radiation (13) on the target (22). Again, by comparing the photocurrent generated by the various photosensitive areas on the surface of the directionally sensitive device(s)(28)(43), directional change in two axis (25) can be detected and an electromagnetic beam position signal (30)(44) can be generated.

The electromagnetic beam position signal (30)(44) can be analyzed by a control system (45), as further discussed below, and a position correction signal (46) can be transmitted to at least one position control device (23) coupled to the adjustable optical element(s)(24) or focal element (21). The position control device(s) can provide independent axes of motion control allowing nanometer position correction of the adjustable optical element(s) with a precision of about 30 nanometers. For example, a motorized center mount and multiaxis driver with an XYZ translation stage as manufactured by New Focus, Inc. 2630 Walsh Avenue, Santa Clara, Calif. (e.g. part nos. 8882 and 8732) can be used as a position control device (23). See also, Nano-Motion System Performs Closed Loop Control of Picomotors, Automation View, Vol. 6, No. 2, 10 (2001). By adjusting the position of the adjustable optical element(s) (24), the electromagnetic radiation beam can be directionally controlled to maintain alignment with an existing target location or to establish alignment with a new target location.

Now referring primarily to FIGS. 1 and 3, certain embodiments of the invention can further comprise an image representation capture device (31) such as a charge coupled device (CCD) camera can be used to capture a representation of an image (32) of the fluid stream (7) established below the tip of the nozzle (8) and any fluorescence or scatter emission (15) generated by the target (22), such as a particle (4), within the fluid stream (7) on an image screen (33).

An illumination source (47) may direct electromagnetic emissions within a known wavelength band towards the flow cytometer target area (22). The purpose of this illumination may be to project an image of the fluid stream (7) at the target area (22) onto the image screen (33) in the image plane of a focal element (21). The wavelength band of this illumination source (47) can be significantly removed, so as not to interfere, from any of the wavelength bands of interest for the purposes of analyzing the target (22) or particle (4). This illumination source (47) may remain enabled simultaneously with irradiation of a target (22) or particle(4) in the fluid stream (7).

The image screen (33) can further comprise a single or plurality of image screen apertures (34) on which the beam of fluorescence or scatter emission (15) from the target (22) can be aligned. The travel direction of the beam of fluorescent or scatter emission can be assessed by determining that portion of the aperture area (35) through which the beam of fluorescent or scatter emission (15) does not pass through.

A plurality of beams of electromagnetic radiation can be targeted on the fluid stream (7) to interrogate a single particle (4) entrained within the fluid stream (7) a plurality of times. As such, a single or a plurality of wavelength selective or filtering elements (28) may be placed between the image (32) and the imaging device (31) to afford wavelength selection of the imaged scatter or fluorescence emission (15).

An image signal (36) can be stored in the memory storage element (30) and then retrieved, and analyzed using software or other algorithms to calibrate, monitor change, and modify the actual conditions at the target (22) through feedback control as disclosed by WO 99/44037, incorporated by reference herein.

In order to enable precise positioning of the electromagnetic radiation beam (13) at the target area (22), the flow cytometer nozzle (48) can be adjustably mounted in a manner responsive to at least one position control devices (49) such as actuated linear or rotary translation stages. The position control devices (23)(49) can then receive a position correction signal (46) to return or maintain the fluid stream in the correct position to align the target (22) with the electromagnetic radiation beam or to align the scatter or flourescent emission (15) with the apertures of the image screen and the receiver (14).

Again referring primarily to FIG. 1, in certain embodiments of the invention an additional image representation capture device (37) such as a CCD camera may be utilized to view the target area (perhaps co-axially with the path of the electromagnetic radiation beam (13) through the focal element (21) used to concentrate the beam of electromagnetic radiation (13) on the target (22) particles to be analyzed. The position of the focal element (21) may be controlled by a position control device(s)(23) so that position and direction of both the imaged radiation emission path (39) and the path of the beam of electromagnetic radiation (13) can be directionally controlled simultaneously.

Imaging can be achieved by use of a radiation polarization element (40) such as a retarder/waveplate to alter the state of polarization of the path of the beam of electromagnetic radiation (13), and a polarization sensitive reflecting element (41). The polarization sensitive reflecting element (41) may be used to reflect a variable portion of the beam of electromagnetic radiation (13) to a position sensitive device (50), this proportion being dependent on the position or orientation of the radiation polarization element (40).

Now referring primarily to FIGS. 4 and 5, a controlling device or control system (45) may be responsive to each directional signal (30)(44)(51) generated by each directionally sensitive device (28)(43)(50) and responsive to each image signal (36)(52) generated by each imaging device (31)(37) which can be stored in at least one memory storage element (30) and can be periodically retrieved and analyzed by the control system (45). A controller (53) provides position correction signals (46) to the position control devices (46)(49)(23). See also, for example, WO 01/28700 A1, hereby incorporated by reference herein.

Now referring primarily to FIG. 5, one embodiment of a flow chart for an alignment algorithm is shown where a sequence of steps are performed by a computer or other electronic device (54) in order to monitor and control a flow cytometer alignment system. The first step can be calibrating and storing initial operating parameters (56) before the feedback control algorithm is enabled as those familiar in the art would expect. An enabling step (57) initiates the control algorithm (58) to accept and analyze position signals (59) to determine alignment error and to transmit position correction signals (60) to the various position control devices (23)(49) to positionally control alignment of the various radiation beam paths (13)(15) as discussed above. The alignment control system can disable (62) the flow cytometer, if alignment of the various radiation beam paths (13)(15) cannot be achieved.

As can be easily understood from the foregoing, the basic concepts of the present invention may be embodied in a variety of ways. It involves various embodiments of alignment and monitoring systems. In this patent application, the methods and techniques used with the alignment and monitoring systems are disclosed as part of the results shown to be achieved by the various devices described and as steps that are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this National Phase patent application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function can be accomplished by a device, subroutine, or program. Apparatus claims may not only be included for the devices described, but also method or process claims may be included to address the functions the invention and each element performs. Neither the description nor the terminology is intended to limit the scope of the claims.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "image" should be understood to encompass disclosure of the act of "imaging"—whether explicitly discussed or not—and, conversely, were there only disclosure of the act of "imaging", such a disclosure should be understood to encompass disclosure of an "image" and even a "means for imaging". Such changes and alternative terms are to be understood to be explicitly included in the description. Additionally, the various combinations and permutations of all elements or applications can be created and presented. All can be done to optimize the design or performance in a specific application.

Any acts of law, statutes, regulations, or rules mentioned in this application for patent; or patents, publications, or other references mentioned in this application for patent, are each hereby incorporated by reference. Specifically, U.S. Provisional Patent Application No. 60/291,736, filed May 17, 2001, is hereby incorporated by reference including any figures or attachments, and each of the references in any information disclosure statement filed with this application are hereby incorporated by reference.

In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. However, as to each of the above, to the extent that such information or statements incorporated by reference might be considered inconsistent with the patenting of this/these invention(s) such statements are expressly not to be considered as made by the applicant(s).

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

Thus, the applicant(s) should be understood to have support to claim at least: i) each of the flow cytometer optical alignment systems as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, and x) the various combinations and permutations of each of the elements disclosed.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the subject matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The invention claimed is:

1. A flow cytometer optical alignment system, comprising:
   a. a target;
   b. an electromagnetic radiation emission source;
   c. an electromagnetic radiation beam emitted from said electromagnetic radiation emission source directionally responsive to at least one optical element;
   d. a electromagnetic radiation beam direction sensor having a surface located to receive a portion of said electromagnetic radiation beam, wherein incidence of said portion of said electromagnetic radiation beam on said surface generates an electromagnetic radiation beam position signal; and
   e. a position control device coupled to said at least one optical element, wherein said position control device responds to an electromagnetic radiation beam direction correction signal to directionally control said optical element to align said electromagnetic radiation beam.

2. A flow cytometer optical alignment system as described in claim 1, wherein said electromagnetic radiation beam direction sensor samples a portion of said electromagnetic radiation beam at a location between said at least one optical element and said target.

3. A flow cytometer optical alignment system as described in claim 1, wherein said electromagnetic radiation beam direction sensor samples a portion of said electromagnetic radiation beam after incidence of said electromagnetic radiation beam on said target.

4. A flow cytometer optical alignment system as described in claim 2 or 3, wherein said electromagnetic radiation beam direction sensor comprises a quadrant photodiode sensor.

5. A flow cytometer optical alignment system as described in claim 1, further comprising a fluid stream, wherein said target comprises a location in said fluid stream, and wherein said electromagnetic radiation beam aligns with said location in said fluid stream.

6. A flow cytometer optical alignment system as described in claim 5, further comprising particles entrained in said fluid stream, wherein said electromagnetic radiation beam aligned with said location in said fluid stream irradiates at least one of said particles entrained in said fluid stream.

7. A flow cytometer optical alignment system as described in claim 1, further comprising a nozzle having a nozzle aperture, wherein said fluid stream exits through said nozzle aperture.

8. A flow cytometer optical alignment system as described in claim 7, further comprising:
   a. a second optical element to which said electromagnetic radiation beam emitted from said electromagnetic radiation emission source is directionally responsive;
   b. a second electromagnetic radiation beam direction sensor having a surface positioned to receive a portion of said electromagnetic radiation beam, wherein incidence of said portion of said electromagnetic radiation beam on said surface generates an electromagnetic radiation beam direction correction signal; and
   c. a second optical orientation element coupled to said at least one optical element, wherein said second optical orientation element responds to said electromagnetic radiation beam direction correction signal to automatically align said electromagnetic radiation beam on said target.

9. A flow cytometer optical alignment system as described in claim 7, wherein said electromagnetic radiation beam direction sensor samples a portion of said electromagnetic radiation beam at a location between said at least one optical element and said target.

10. A flow cytometer optical alignment system as described in claim 1, wherein said electromagnetic radiation beam direction sensor samples a portion of said electromagnetic radiation beam after incidence of said electromagnetic radiation beam on said target.

11. A flow cytometer optical alignment system as described in claim 1, further comprising:
    a. a electromagnetic radiation polarization element;
    b. a beam of electromagnetic radiation emitted from said target coaxial to said excitation path responsive to said electromagnetic radiation polarization element;
    c. a polarization sensitive reflecting element that reflects said beam of electromagnetic radiation emitted from said target polarized by said electromagnetic radiation polarization element; and
    d. an image representation capture device responsive to said electromagnetic radiation emitted from said target polarized by said electromagnetic radiation polarization element.

12. A flow cytometer optical alignment system as described in claim 1, further comprising:
    a. an illumination element positioned to provide illumination of said fluid stream;
    b. an electromagnetic radiation emission generated by said particle;
    b. an image screen incident to said electromagnetic radiation emission generated by said particle and said illumination of said fluid stream;
    c. an image generated on said image screen of said electromagnetic radiation emission generated by said particle and said illumination of said fluid stream;
    d. at least one image screen aperture through which at least part of said electromagnetic radiation emission generated by said particle passes;
    e. a receiver incident to said at least part of said electromagnetic radiation emission generated by said particle; and
    f. an image representation capture device responsive to said image generated on said image screen, wherein said image representation capture device generates a electromagnetic radiation beam position signal.

13. A flow cytometer optical alignment system as described in claim 1, further comprising:
    a. at least one memory storage element responsive to said electromagnetic beam position signal;
    b. a retrieval element to retrieve said electromagnetic beam position signal from said at least one memory storage element;
    c. an electromagnetic beam position signal analysis element; and
    d. a controller that provides electromagnetic radiation beam position correction signal to position control devices coupled to said at least one optical element.

14. A flow cytometer, comprising:
a. a nozzle having an nozzle aperture;
b. a fluid stream which exits said nozzle through said nozzle aperture;
c. a droplet generator to which said fluid stream responds by forming droplets, wherein said droplets have a break off point a distance from said nozzle aperture;
d. electromagnetic radiation beam having a path through said fluid stream between said nozzle aperture and said break off point;
e. at least one optical element to which said electromagnetic radiation beam is directionally responsive;
f. a electromagnetic radiation beam position sensor having a surface located to receive a portion of said electromagnetic radiation beam, wherein incidence of said portion of said electromagnetic radiation beam on said surface generates an electromagnetic radiation beam position signal; and
g. a position control device coupled to said at least one optical element, wherein said position control device responds to an electromagnetic radiation beam direction correction signal to directionally control said optical element to align said electromagnetic radiation beam.

15. A method of controlling the direction of an electromagnetic radiation beam of a flow cytometer, comprising the steps of:
a. emitting an electromagnetic radiation beam directionally responsive to an optical element;
b. sampling a portion of said electromagnetic radiation beam to a surface positionally sensitive to incidence of said electromagnetic radiation beam;
c. generating an electromagnetic radiation beam position signal corresponding to position of said incidence of said electromagnetic radiation beam on said surface;
d. analyzing said electromagnetic radiation beam position signal;
e. determining alignment error of said electromagnetic radiation beam to a target;
f. generating an electromagnetic radiation beam direction correction signal; and
g. adjusting said optical element to correct alignment error of said electromagnetic beam with a target location.

16. A method of controlling the direction of an electromagnetic radiation beam of a flow cytometer as described in claim 15, further comprising the step of streaming a fluid through said target location.

17. A method of controlling the direction of an electromagnetic radiation beam of a flow cytometer as described in claim 15, further comprising the step of entraining at least one particle in said fluid, wherein said electromagnetic radiation beam irradiates said particle at said target location.

* * * * *